(12) United States Patent
Okuno et al.

(10) Patent No.: US 9,968,368 B2
(45) Date of Patent: May 15, 2018

(54) DRILL GUIDE

(71) Applicants: TEIJIN MEDICAL TECHNOLOGIES CO., LTD, Osaka (JP); NATIONAL UNIVERSITY CORPORATION KOBE UNIVERSITY, Hyogo (JP)

(72) Inventors: Masaki Okuno, Osaka (JP); Hiroshi Morii, Osaka (JP); Katsuya Nada, Osaka (JP); Ryosuke Kuroda, Hyogo (JP)

(73) Assignees: TEIJIN MEDICAL TECHNOLOGIES CO., LTD., Osaka (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 713 days.

(21) Appl. No.: 14/548,402

(22) Filed: Nov. 20, 2014

(65) Prior Publication Data

US 2015/0182235 A1 Jul. 2, 2015

(30) Foreign Application Priority Data

Nov. 22, 2013 (JP) .................................. 2013-241761

(51) Int. Cl.
*A61B 17/17* (2006.01)
(52) U.S. Cl.
CPC ................................ *A61B 17/1714* (2013.01)
(58) Field of Classification Search
CPC .. A61B 17/1714; A61B 17/17; A61B 17/1764
See application file for complete search history.

(56) References Cited

U.S. PATENT DOCUMENTS

| 6,342,057 B1 | 1/2002 | Brace et al. |
| 2006/0106399 A1* | 5/2006 | Taras ..................... A61B 17/17 606/96 |
| 2009/0299416 A1 | 12/2009 | Hanni et al. |
| 2010/0151411 A1 | 6/2010 | Suter et al. |

FOREIGN PATENT DOCUMENTS

| JP | 2003-531666 | 10/2003 |
| JP | 2006-102002 | 4/2006 |
| JP | 2009-511136 | 3/2009 |
| JP | 2010-115261 | 5/2010 |
| JP | 2010-137050 | 6/2010 |

* cited by examiner

*Primary Examiner* — Andrew Yang
(74) *Attorney, Agent, or Firm* — Wenderoth, Lind & Ponack, L.L.P.

(57) ABSTRACT

A drill guide has a main body in which a drill insertion hole is formed and plural projection portions to be inserted into plural bone tunnels. The plural projection portions project forward from the main body parallel with the center line of the drill insertion hole, a virtual drill insertion hole which extends from the drill insertion hole of the main body is formed between the plural projection portions parallel with their center lines by cutting out confronting portions of the plural projection portions, and the length of at least one of the drill insertion hole and the virtual drill insertion hole is 5 mm or more. The drill guide can guide a drill so as to be correctly between plural bone tunnels bored through a living body bone without causing axis deviation so that a link bone tunnel for connecting the plural bone tunnels can be formed between them in the same direction as their direction.

7 Claims, 9 Drawing Sheets

DRILL GUIDE

BACKGROUND OF THE INVENTION

1. Technical Field

The present invention relates to a drill guide for guiding a drill to be used for forming, between plural bone tunnels, a link bone tunnel for connecting the plural bone tunnels. More specifically, the present invention relates to a drill guide which is suitably used for forming a bone tunnel having a rectangular or elliptical opening that is suitable to transplant a tendon acquired from another part in the knee joint or the like in, for example, reconstruction of a torn anterior cruciate ligament.

2. Description of the Related Art

As is well known, in reconstruction of a torn anterior cruciate ligament (ACL), it is necessary to bore, through a bone of the knee joint at a proper location, a bone tunnel that is necessary to transplant a tendon acquired from another part in the knee joint. A common method that has been employed so far for this purpose is to bore a circular bone tunnel through a bone of the knee joint at a proper location by a hollow drill, insert a bone piece of an end portion of a transplantation tendon into the circular bone tunnel, and fix the bone piece to the bone with fixing screws.

However, for a circular bone tunnel, when a bone piece of a transplantation tendon is inserted, the stability (i.e., fitting) of the inserted bone piece is low. The present inventors have proposed forming a bone tunnel having a rectangular or elliptical opening that is high in conformity to the surface of a bone piece of a transplantation tendon by forming plural (two) circular bone tunnels, connecting them by forming a link bone tunnel between them using a drill, and then expanding a connected bone tunnel with a dilator into a rectangular or elliptical shape or cutting with a chisel.

Incidentally, as a drill guide for guiding a drill for cutting between plural bone tunnels, known is a guide member for a dental drill whose end face has a cutting blade (JP-A-2006-102002). This guide member is used in forming, in the jaw bone, using the above dental drill, a tunnel corresponding to a regenerated tooth root of double root which has two branch roots. The guide member includes an elliptical plate-like portion for covering two adjoining holes, leg pieces disposed at the two respective ends of the plate-like portion and to be inserted into the two respective holes, and a drill insertion hole provided in the center of the plate-like portion Also known is a surgical drill guide assembly which includes alignment drill pipes for receiving and guiding surgical drill bits, a bushing having an expandable front end portion which supports the alignment drill pipes, and a drill guide assembly handle which is connected to the bushing (JP-T-2003-531666). The front end portion of the bushing is expanded in a bone plate, whereby the bushing is locked being spaced from bone plate fastener holes and the alignment drill pipes are aligned with corresponding fastener holes.

SUMMARY OF THE INVENTION

In the guide member of JP-A-2006-102002, the plate-like portion is fixed by inserting the leg pieces into two holes formed in the jaw bone and cutting is performed as a dental drill that is inserted into the drill insertion hole formed in the plate-like portion is guided so as to be between the two holes. However, the penetration dimension (depth) of the drill insertion hole formed in the plate-like portion is small and no support portion such as a wall that surrounds the dental drill is formed around the drill insertion hole. These result in problems that the dental drill is prone to deviation of its axis and it is difficult to guide the dental drill properly while maintaining its direction. Therefore, it is difficult to use this guide member as a drill guide for forming a link bone tunnel (through-hole) between two bone tunnels that penetrate through a living body bone in, for example, ACL reconstruction.

The drill guide assembly of JP-T-2003-531666 serves to guide a surgical drill(s) in forming one or plural bone tunnels also using a bone plate having slots and fastener holes. This drill guide assembly is not for guiding a surgical drill so that it is between plural bone tunnels in boring a link bone tunnel between the plural bone tunnels.

The present invention has been made in the above circumstances, and an object of the present invention is therefore to provide a drill guide which can guide a drill so as to be between plural bone tunnels bored through a living body bone correctly without causing axis deviation so that a link bone tunnel for connecting the plural bone tunnels can be formed between them in the same direction as they extend in, for example, ACL reconstruction.

To attain the above object, a drill guide according to the present invention is a drill guide for guiding a drill to be used for forming, between a plurality of bone tunnels, a link bone tunnel for connecting the plurality of bone tunnels, which includes:

a main body in which a drill insertion hole is formed; and a plurality of projection portions to be inserted into the plurality of bone tunnels, wherein the plurality of projection portions project forward from the main body parallel with a center line of the drill insertion hole, a virtual drill insertion hole which extends from the drill insertion hole of the main body is formed between the plurality of projection portions parallel with center lines of the plurality of projection portions by cutting out confronting portions of the plurality of projection portions, and a length of at least one of the drill insertion hole and the virtual drill insertion hole is 5 mm or more.

In a drill guide according to the present invention, it is desirable that outer diameters of the plurality of projection portions are equal to diameters of the drill insertion hole and the virtual drill insertion hole.

It is also desirable that the virtual drill insertion hole overlaps with the plurality of projection portions over a length that is greater than or equal to ¼ of diameters of the plurality of projection portions.

It is also desirable that the drill guide according to claim 1, wherein lengths of the plurality of projection portions are 15 mm or more.

It is further desirable that a through-hole in which to insert a pin is formed continuously in the plurality of projection portions and the main body.

The drill guide according to the present invention makes it possible to, in ACL reconstruction for example, form a link bone tunnel that connects plural bone tunnels by inserting the plural projection portions into the plural (two) bone tunnels bored through a bone of the knee joint or the like to fix the main body; and inserting a drill into the virtual drill insertion hole located between the projection portions from the drill insertion hole of the main body so as to guide the drill between the plural bone tunnels. In this regard, the drill guide according to the present invention is configured in such a manner that the projection portions to be inserted into the plural respective bone tunnels project parallel with the center line of the drill insertion hole of the main body and the virtual drill insertion hole which extends from the drill insertion hole is formed parallel with the center lines of the projection portions. Therefore, the drill can be guided parallel with the plural bone tunnels by the drill insertion hole and the virtual drill insertion hole. Since the virtual drill insertion hole is formed by cutting out confronting portions of the projection portions, the drill that has been inserted into the virtual drill insertion hole located between the projection portions from the drill insertion hole of the main body is supported without axis deviation axis by means of the inner surface of the drill insertion hole and the projection portions located on the two respective sides of the virtual drill insertion hole. Furthermore, since the length of at least one of the drill insertion hole and the virtual drill insertion hole is set to be 5 mm or more, the drill can be guided so as to be between the plural bone tunnels in such a manner that axis deviation is suppressed reliably.

In a drill guide according to the present invention in which the outer diameters of the plural projection portions are equal to the diameters of the drill insertion hole and the virtual drill insertion hole, plural bone tunnels can be connected to each other by forming, between them, a link bone tunnel having the same diameter as their diameters by inserting a drill having the same diameter as the outer diameters of the projection portions into the virtual drill insertion hole from the drill insertion hole. Thus, there is an advantage that by thereafter subjecting the connected bone tunnel to chiseling or expansion using a dilator, a rectangular or elliptical bone tunnel can be formed easily into which a bone piece of a tendon for transplantation can be inserted stably.

In a drill guide according to the present invention in which the virtual drill insertion hole overlaps with the plural projection portions over a length that is greater than or equal to ¼ of the diameters of the plural projection portions, a link bone tunnel can be formed between plural bone tunnels so as to overlap with each bone tunnel over a length that is greater than or equal to ¼ of the diameters of the plural bone tunnels by a drill that is inserted into the virtual drill insertion hole from the drill insertion hole of the main body. Thus, there is an advantage that a bone tunnel having a rectangular or elliptical opening can be formed easily by chiseling or expansion using a dilator. There is also another advantage that the drill that is inserted in the virtual drill insertion hole can be supported reliably by the plural projection portions without suffering axis deviation.

A drill guide according to the present invention in which the lengths of the plural projection portions are greater than or equal to 15 mm provides an advantage that the main body can be fixed reliably by inserting the projection portions into the plural bone tunnels.

Furthermore, a drill guide according to the present invention in which a through-hole in which to insert a pin is formed continuously in the main body and the plural projection portions provides the following advantage. As described later, where guide pins remain that were used in boring plural bone tunnels in a bone of the knee joint or the like using hollow drills, the plural projection portions of the drill guide can be guided to the plural respective bone tunnels and inserted into them easily by inserting the guide pins into the respective through-holes.

DETAILED DESCRIPTION OF THE INVENTION

A drill guide according to an embodiment of the present invention will be hereinafter described in detail with reference to the drawings.

Figure 1:
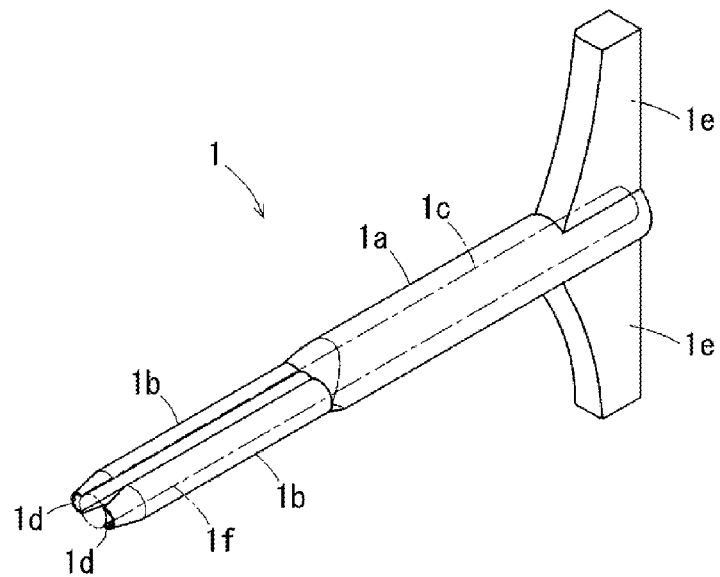
FIG. 1 is a perspective view of a drill guide according to an embodiment of the invention.
Figure 2:
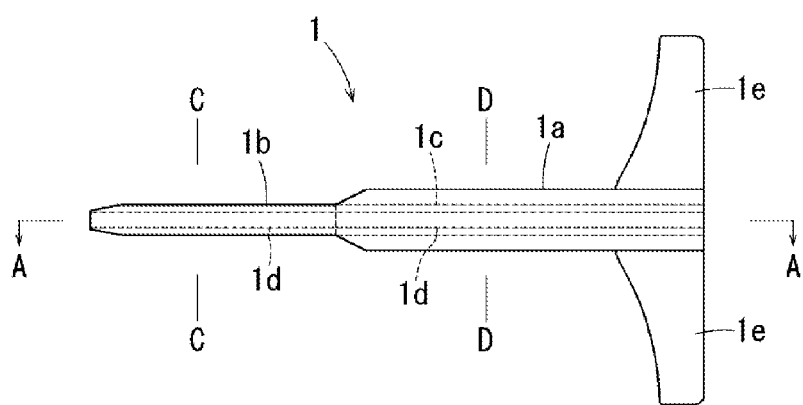
FIG. 2 is a side view of the drill guide.
Figure 3:
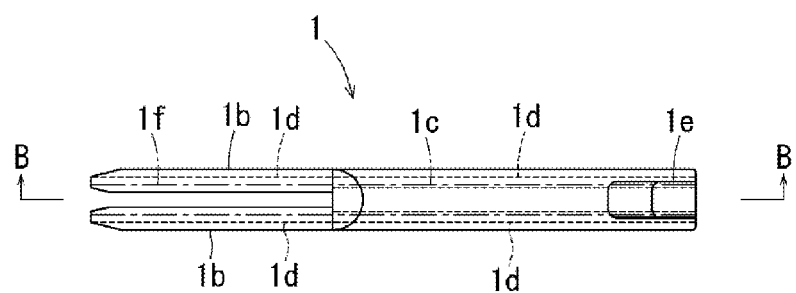
FIG. 3 is a plan view of the drill guide.
Figure 4:
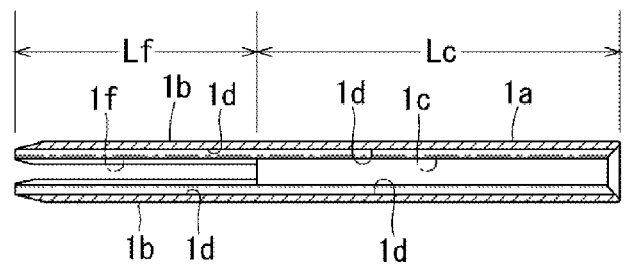
FIG. 4 is a sectional view taken along line A-A in FIG. 2.
Figure 5:
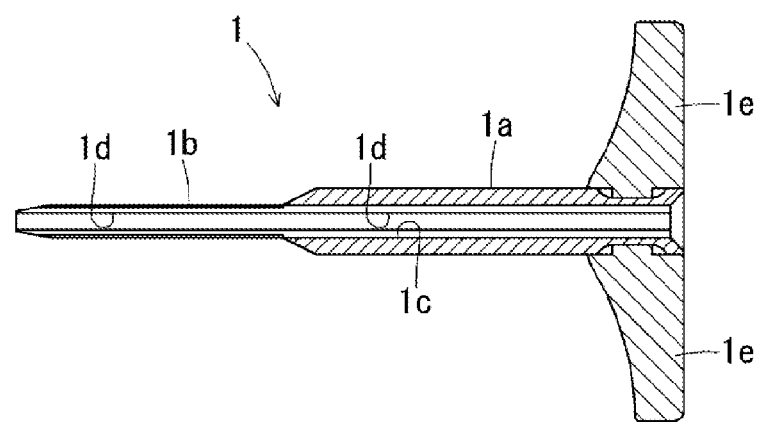
FIG. 5 is a sectional view taken along line B-B in FIG. 3.
Figure 6:
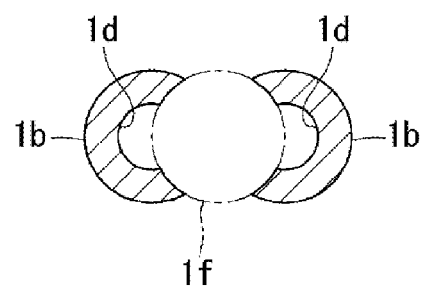
FIG. 6 is an enlarged end view of cutting FIG. 2 along line C-C.
Figure 7:
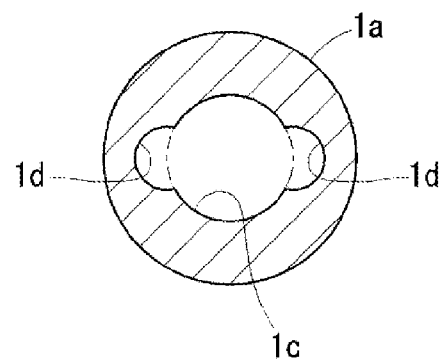
FIG. 7 is an enlarged end view of cutting FIG. 2 along line D-D.
Figure 8:
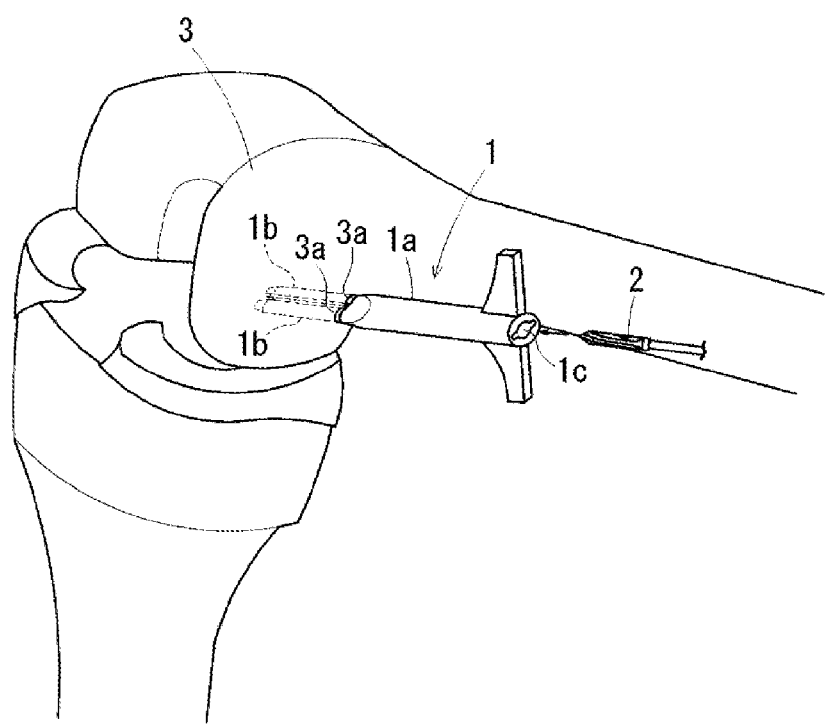
FIG. 8 is a perspective view showing a state that the drill guide is in use.

FIG. 1 is a perspective view of the drill guide according to the embodiment of the invention, FIG. 2 is a side view of the drill guide, FIG. 3 is a plan view of the drill guide, FIG. 4 is a sectional view taken along line A-A in FIG. 2, FIG. 5 is a sectional view taken along line B-B in FIG. 3, FIG. 6 is an enlarged end view of cutting FIG. 2 along line C-C, FIG. 7 is an enlarged end view of cutting FIG. 2 along line D-D, and FIG. 8 is a perspective view showing a state that the drill guide is in use.

The drill guide 1 shown in FIGS. 1-8 is used for connecting plural circular bone tunnels formed through a bone of the knee joint or the like by forming a link bone tunnel between them in a step that is executed before formation, in the bone of the knee joint or the like, of a rectangular or elliptical bone tunnel that is suitable to transplant a tendon acquired from another part in the knee joint or the like in, for example, reconstruction of a torn anterior cruciate ligament (ACL). As shown in the figures, the drill guide 1 includes a cylindrical main body 1a and plural (two) projection portions 1b, 1b to be inserted in plural respective bone tunnels.

As shown in FIGS. 5 and 7, a drill insertion hole 1c penetrates through the cylindrical main body 1a along its center line. Through-holes 1d, 1d through which to insert guide pins 4f, 4f as described later are formed parallel with each other on the two respective sides of the drill insertion hole 1c so as to be parts of the drill insertion hole 1c. Grip portions 1e, 1e are attached to a rear end portion of the main body 1a so as to project upward and downward, respectively, by such means as welding to make it possible to push the projection portions 1b, 1b strongly into the plural respective bone tunnels by gripping the grip portions 1e, 1e.

The projection portions 1b, 1b project forward from the cylindrical main body 1a parallel with the center line of the drill insertion hole 1c so as to be left-right symmetrical with respect to the center line of the drill insertion hole 1c. Through-holes 1d, 1d through which to insert the guide pins 4f, 4f as described later are formed along the center lines of the projection portions 1b, 1b, respectively, so as to be continuous with the respective through-holes 1d, 1d that are formed in the main body 1a on the two respective sides of the drill insertion hole 1c. Tip portions of the projection portions 1b, 1b are tapered so that they can be inserted into plural respective bone tunnels easily.

As shown in FIGS. 4 and 6, in the cylindrical projections 1b, 1b in which the through-holes 1d, 1d are formed, a virtual drill insertion hole 1f which is an extension of the drill insertion hole 1c of the main body 1a is formed parallel with the center lines of the projection portions 1b, 1b by cutting out confronting portions of the projection portions 1b, 1b. Slits are formed in the cut-out confronting portions of the projection portions 1b, 1b. Therefore, when a drill is inserted into the virtual drill insertion hole if from the drill insertion hole 1c, the drill is guided parallel with the projection portions 1b, 1b (in other words, parallel with plural bone tunnels through which the respective projection portions 1b, 1b are inserted) and supported by the inner surface of the drill insertion hole 1c and the projection portions 1b which are located on the two respective sides of the virtual drill insertion hole if so as not to cause axis deviation.

At least one of the length Lf of the virtual drill insertion hole 1f (i.e., the length Lf of the cut-out confronting portions of the projection portions 1b, 1b) and the length Lc of the drill insertion hole 1c of the main body 1a needs to be set to be 5 mm or more. This allows at least one of the drill insertion hole 1c and the pair of side projection portions 1b, 1b which are located on the two respective sides of the virtual drill insertion hole 1f, to suppress axis deviation. The lengths Lf and Lc have no particular upper limits, and the effect of suppressing the deviation of the axis of a drill is enhanced as they increase. However, the lengths Lf and Lc are too great, the drill guide becomes so large as to be difficult to handle. It is therefore desirable to set the upper limits of the lengths Lf and Lc to 30 to 50 mm and 50 to 70 mm, respectively.

In the embodiment, the length Lf of the virtual drill insertion hole 1f is equal to the lengths of the projection portions 1b, 1b because the virtual drill insertion hole if is formed by cutting out the confronting portions of the projection portions 1b, 1b over the entire length of the projection portions 1b, 1b. However, the length Lf of the virtual drill insertion hole if is determined by the length over which the confronting portions of the projection portions 1b, 1b are cut out and hence does not necessarily coincide with the length of the projection portions 1b, 1b.

It is preferable that the diameters of the drill insertion hole 1c and the virtual drill insertion hole 1f are set equal to the outer diameters of the projection portions 1b, 1b. In this case, plural bone tunnels can be connected to each other by forming, between them, a link bone tunnel having the same diameter as their diameter by inserting a drill having the same diameter as the outer diameters of the projection portions 1b, 1b into the virtual drill insertion hole 1f from the drill insertion hole 1c. Therefore, by thereafter doing chiseling or expansion using a dilator, a rectangular or elliptical bone tunnel can be formed easily into which a bone piece of a tendon for transplantation can be inserted stably.

It is desirable that the virtual drill insertion hole 1f and the projection portions 1b, 1b are formed so that the virtual drill insertion hole if overlaps with the projection portions 1b, 1b over a length that is greater than or equal to ¼ of the diameters of each projection portion 1b, 1b. In this case, a link bone tunnel can be formed between plural bone tunnels so as to overlap with bone tunnels over a length that is greater than or equal to ¼ of the diameters of the bone tunnel by a drill that is inserted into the virtual drill insertion hole if from the drill insertion hole 1c. Therefore, by thereafter doing chiseling or the like, a rectangular or elliptical bone tunnel can be formed easily. Furthermore, the drill that is inserted in the virtual drill insertion hole 1f can be supported reliably by the projection portions 1b, 1b without suffering deviation of its axis.

There is no particular upper limit on the overlap length of the virtual drill insertion hole 1f and the projection portions 1b, 1b. However, if the overlap length is too great, a bone tunnel formed becomes close to a circle in cross section and the fixing of a bone piece of a transplantation tendon is made less stable. Therefore, it is appropriate to set the upper limit of the overlap length to about ¾ of the diameters of the projection portion 1b, 1b. In particular, it is preferable to form the virtual drill insertion hole if and the projection portions 1b, 1b so as to have an overlap length that is equal to ½ of the outer diameters of the projection portions 1b, 1b because in this case a rectangular or elliptical bone tunnel is formed which has an aspect ratio 1:2 and provides high stability of fixing of a bone piece of a transplantation tendon.

There are no particular limitations on the length of the projection portions 1b, 1b. However, to allow the projection portions 1b to be inserted into plural bone tunnels for fixing reliably the main body 1a and fixed reliably to the bone, it is desirable that the length of the projection portions 1b, 1b is 15 mm or more. For example, taking into consideration the depth (length) of plural bone tunnels that are formed through a thighbone bottom portion of the knee joint in ACL reconstruction, it is desirable to set the upper limit of the length of the projection portions 1b, 1b to 30 to 50 mm.

There are no limitations on the material of the drill guide 1. However, it is desirable that the drill guide 1 is made of a metal that does not adversely affect living body bones, such as titanium or stainless steel.

In, for example, ACL reconstruction, as shown in FIG. 8, the drill guide 1 having the above configuration is used in forming a link bone tunnel in the following manner. The projection portions 1b, 1b are inserted into plural respective bone tunnels 3a, 3a that are bored through a thighbone bottom portion 3 of the knee joint, whereby the main body 1a is fixed to the thighbone bottom portion 3. And the drill guide 1 guides a drill 2 so that it is between the bone tunnels 3a, 3a as it is inserted into the virtual drill insertion hole located between the projection portions 1b from the drill insertion hole 1c of the main body 1a.

The plural bone tunnels 3a, 3a are bored through the thighbone bottom portion 3 in the following manner.

Figure 9:
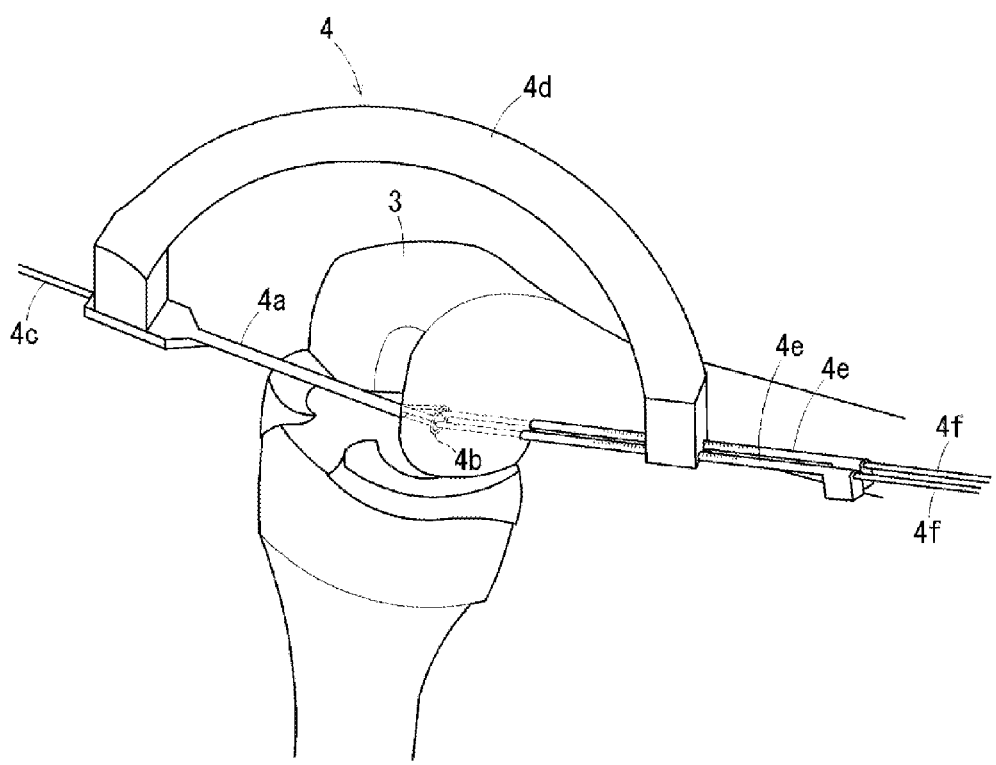
FIG. 9 is a perspective view showing a state that a thighbone bottom portion of the knee joint is pierced by plural guide pins using a guide pin piercing jig in ACL reconstruction.

A guide pin piercing jig 4 as show in FIG. 9 is used. First, a boring aiming portion 4b which is a tip portion of a first cylinder unit 4a is put on a portion, from which to bore bone tunnels, of a concave-curved surface of the thighbone bottom portion 3 and a fixing pin 4c is inserted into the first cylinder unit 4a and stuck through the concave-curved surface of the thighbone bottom portion 3 from behind, whereby the first cylinder unit 4a is fixed tentatively.

Subsequently, the first cylinder unit 4a is attached to one end portion of a curved frame 4d. Two second cylinders 4e, 4e are inserted into two respective insertion holes formed through the other end portion of the curved frame 4d and tip portions of the second cylinders 4e, 4e are stuck into the thighbone bottom portion 3 obliquely from behind. Two guide pins 4f, 4f are inserted into the respective second cylinders 4e, 4e and are caused to pierce the thighbone bottom portion 3 until the tips of the guide pins 4f, 4f reach the boring aiming portion 4b of the first cylinder unit 4a.

Figure 10:
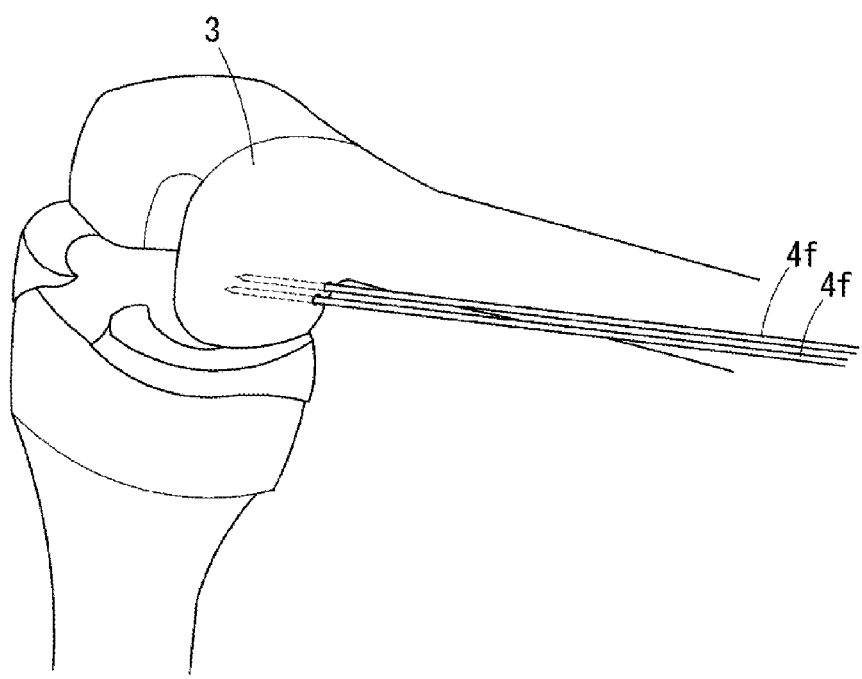
FIG. 10 is a perspective view showing the plural guide pins that have pierced the thighbone bottom portion of the knee joint.
Figure 11:
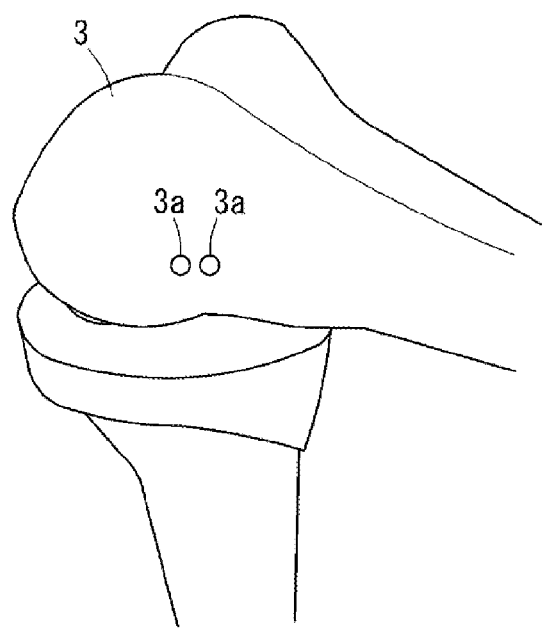
FIG. 11 is a perspective view showing the thighbone bottom portion of the knee joint in which plural bone tunnels are bored.

Then, the first cylinder unit 4a, the fixing pin 4c, the curved frame 4d, and the second cylinders 4e, 4e are removed to leave the guide pins 4f, 4f (see FIG. 10). The guide pins 4f, 4f are inserted into respective hollow drills (not shown), and boring is performed while the hollow drills are guided to a portion, where to bore bone tunnels, of the thighbone bottom portion. Thus, two circular bone tunnels 3a, 3a are formed as shown in FIG. 11.

Figure 12:
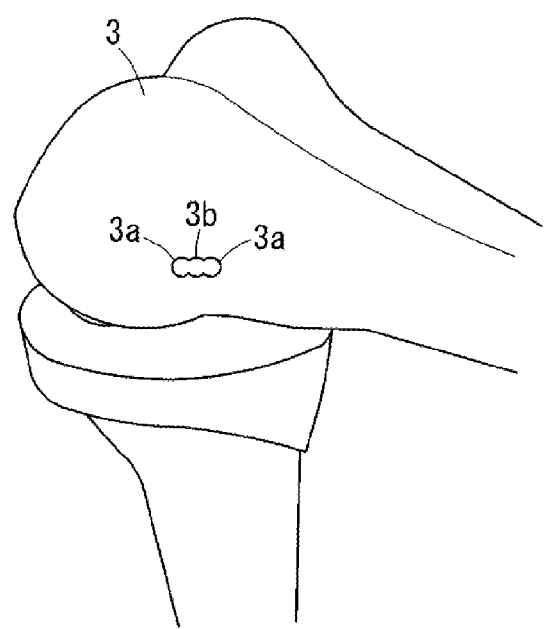
FIG. 12 is a perspective view showing the thighbone bottom portion of the knee joint in which the plural bone tunnels are connected to each other by boring a link bone tunnel between them.

After the two circular bone tunnels 3a, 3a have been formed in the above-described manner, as described with reference to FIG. 8, the projection portions 1b, 1b of the drill guide 1 according to the present invention are inserted into the plural respective bone tunnels 3a, 3a formed through the thighbone bottom portion 3 and the main body 1a is thereby fixed. The bone cutting drill 2 is inserted into the virtual drill insertion hole located between the projection portions 1b, 1b from the drill insertion hole 1c of the main body 1a and cuts the thighbone bottom portion 3 while being guided to as to be between the plural bone tunnels 3a. As a result, as shown in FIG. 12, a link bone tunnel 3b having the same diameter as bone tunnels 3a, 3a is formed between the bone tunnels 3a, 3a so as to overlap with them. Then, the projection portions 1b, 1b are pulled out and the drill guide 1 is removed.

The drill guide 1 according to the present invention is configured in such a manner that the projection portions 1b, 1b project parallel with the center line of the drill insertion hole 1c of the main body 1a, the virtual drill insertion hole 1f which extends from the drill insertion hole 1c is formed between the projection portions 1b, 1b parallel with the center lines of the projection portions 1b, 1b by cutting out confronting portions of the projection portions 1b, 1b, and the length of at least one of the drill insertion hole 1c and the virtual drill insertion hole 1f is 5 mm or more. Therefore, in the above-described work, the drill 2 can be guided parallel with the bone tunnels 3a, 3a. And a link bone tunnel 3b can be formed by guiding the drill 2 so that it is between the bone tunnels 3a, 3a while supporting the drill 2 by means of the inner surface of the drill insertion hole 1c and the projection portions 1b, 1b which are located on the two respective sides of the virtual drill insertion hole 1f, with deviation of the axis of the drill 2 suppressed reliably.

Figure 13:
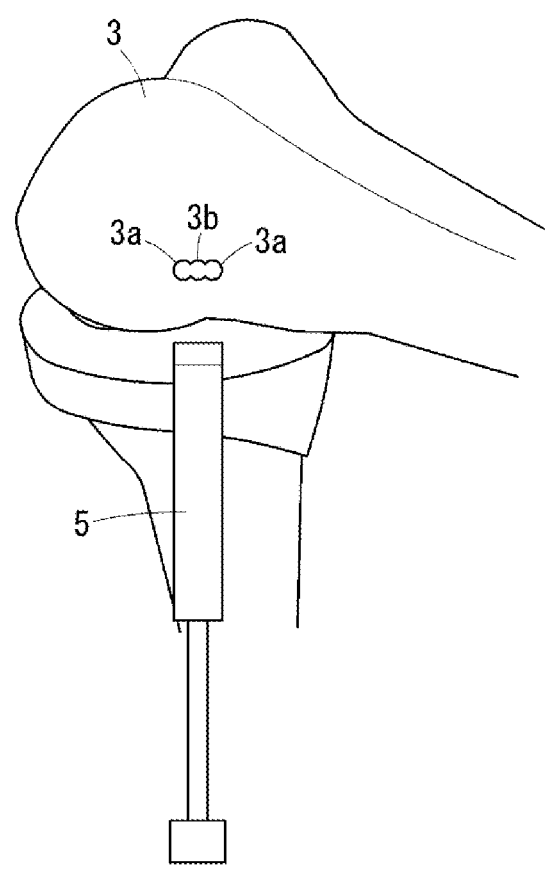
FIG. 13 is a perspective view showing how the continuous bone tunnel formed through the thighbone bottom portion of the knee joint are subjected to cutting with a chisel.
Figure 14:
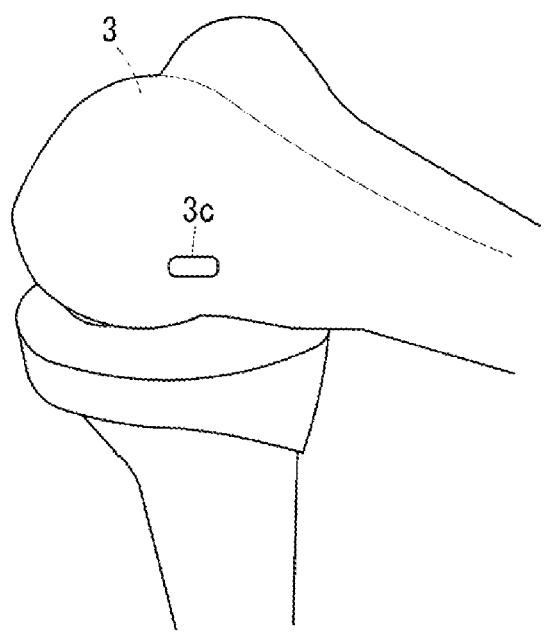
FIG. 14 is a perspective view showing the thighbone bottom portion of the knee joint through which a rectangular or elliptical bone tunnel is formed.

After the bone tunnels 3a, 3a are connected to each other by the link bone tunnel 3b, as shown in FIG. 13 the bone tunnels 3a, 3b, 3a connected to each other are subjected to cutting with a chisel 5 into a rectangular or elliptical shape or expansion with a dilator, whereby a rectangular or elliptical bone tunnel 3c as shown in FIG. 14 which is different from an exisiting circular bone tunnel and suitable for tendon transplantation. Since such a rectangular or elliptical bone tunnel 3c is formed, in the next step an approximately rectangular-parallelepiped-shaped end bone piece of a transplantation tendon acquired from another part can be inserted into the bone tunnel 3c stably. And the end bone piece of the transplantation tendon can be fixed strongly by screwing fixing screws (e.g., made of a polymer that is dissolved in and absorbed by a living body and having no screw head) through the bone piece and the inner surface of the bone tunnel 3c.

In the above example manner of use, the projection portions 1b of the drill guide 1 are directly inserted into the respective bone tunnels 3a of the thighbone bottom portion 3. Where the guide pins 4f, 4f (see FIG. 10) that guided the hollow drills that were used for boring the bone tunnels 3a remain (i.e., are not removed) after the boring of the bone tunnels 3a, 3a, it is possible to insert the guide pins 4f, 4f into the respective through-holes 1d of the drill guide 1 and insert the projection portions 1b, 1b of the drill guide 1 into the respective bone tunnels 3a, 3a in such a manner that the projection portions 1b, 1b are guided by the respective guide pins 4f, 4f, which facilitates the work of inserting the projection portions 1b, 1b.

A manner of use of the drill guide according to the preset invention has been described above for an example case in which a link bone tunnel is formed between plural bone tunnels to connect them to form, in a thighbone bottom portion, a rectangular or elliptical bone tunnel into which a bone piece connected to an end portion of a transplantation tendon can be inserted stably in ACL reconstruction. However, the manner of use of the drill guide according to the present invention is not limited to the above and the drill guide according to the present invention can be applied to every use in which a link bone tunnel is formed between plural bone tunnels.

Although the invention has been described in detail by referring to the particular embodiment, it is apparent to those skilled in the art that various changes and modifications are possible without departing from the spirit and scope of the invention.

The present application is based on Japanese Patent Application No. 2013-241761 filed on Nov. 22, 2013, the disclosure of which is incorporated herein by reference.

The invention claimed is:

1. A drill guide for guiding a drill to be used for forming, between a plurality of bone tunnels, a link bone tunnel for connecting the plurality of bone tunnels, the drill guide comprising:
   a main body in which a drill insertion hole is formed; and
   a plurality of projection portions to be inserted into the plurality of bone tunnels, wherein
   the plurality of projection portions project forward from the main body parallel with a center line of the drill insertion hole,
   a virtual drill insertion hole which extends from the drill insertion hole of the main body is formed between the plurality of projection portions parallel with center lines of the plurality of projection portions by cutting out confronting portions of the plurality of projection portions,
   a length of at least one of the drill insertion hole and the virtual drill insertion hole is 5 mm or more, and
   outer diameters of the plurality of projection portions are equal to diameters of the drill insertion hole and the virtual drill insertion hole.

2. The drill guide according to claim 1, wherein the virtual drill insertion hole overlaps with the plurality of projection portions over a length that is greater than or equal to ¼ of diameters of the plurality of projection portions.

3. The drill guide according to claim 1, wherein lengths of the plurality of projection portions are 15 mm or more.

4. The drill guide according to claim 1, wherein a through-hole in which to insert a pin is formed in each of the plurality of projection portions, the through-holes extending continuously through the main body.

5. A drill guide for guiding a drill to be used for forming, between a plurality of bone tunnels, a link bone tunnel for connecting the plurality of bone tunnels, the drill guide comprising:
- a main body in which a drill insertion hole is formed; and
- a plurality of projection portions to be inserted into the plurality of bone tunnels, wherein
- the plurality of projection portions project forward from the main body parallel with a center line of the drill insertion hole,
- a virtual drill insertion hole which extends from the drill insertion hole of the main body is formed between the plurality of projection portions parallel with center lines of the plurality of projection portions by cutting out confronting portions of the plurality of projection portions,
- a length of at least one of the drill insertion hole and the virtual drill insertion hole is 5 mm or more, and
- a through-hole in which to insert a pin is formed in each of the plurality of projection portions, the through-holes extending continuously through the main body.

6. The drill guide according to claim 5, wherein the virtual drill insertion hole overlaps with the plurality of projection portions over a length that is greater than or equal to ¼ of diameters of the plurality of projection portions.

7. The drill guide according to claim 5, wherein lengths of the plurality of projection portions are 15 mm or more.

* * * * *